US00PP27630P3

(12) United States Plant Patent
Werner et al.

(10) Patent No.: US PP27,630 P3
(45) Date of Patent: Jan. 31, 2017

(54) ***CERCIS* PLANT NAMED 'PINK POM POMS'**

(50) Latin Name: ***Cercis canadensis* and *canadensis* var. *texensis***
Varietal Denomination: Pink Pom Poms

(71) Applicant: North Carolina State University, Raleigh, NC (US)

(72) Inventors: Dennis James Werner, Raleigh, NC (US); Edward Alex Neubauer, Belvidere, TN (US)

(73) Assignee: North Carolina State University, Raleigh, NC (US)

( * ) Notice: Subject to any disclaimer, the term of this patent is extended or adjusted under 35 U.S.C. 154(b) by 118 days.

(21) Appl. No.: 14/544,232

(22) Filed: Dec. 11, 2014

(65) Prior Publication Data

US 2016/0174442 P1 Jun. 16, 2016

(51) Int. Cl.
*A01H 5/02* (2006.01)

(52) U.S. Cl.
USPC ..... Plt./216

(58) Field of Classification Search
USPC ..... Plt./216
See application file for complete search history.

*Primary Examiner* — June Hwu
(74) *Attorney, Agent, or Firm* — Myers Bigel, P.A.

(57) ABSTRACT

*Cercis* 'Pink Pom Poms' is a new and distinct variety of redbud tree that has the following unique combination of desirable features that are outstanding in a new variety including (1) ease of asexual propagation using chip budding, (2) semi-upright growth habit; (3) foliage with glossy green color; (4) bright purple-violet double flowers produced in abundance during the spring; and female structures that are essentially sterile, resulting in no seed pod set.

5 Drawing Sheets

Latin name of the genus and species: The Latin name of the novel plant variety disclosed herein is Genus: *Cercis*, Species: a hybrid between *canadensis* and *canadensis* var. *texensis*.

Variety denomination: The inventive variety of *Cercis* disclosed herein has been given the varietal denomination 'Pink Pom Poms'.

BACKGROUND OF THE INVENTION

The present invention relates to a new and distinct variety of *Cercis* (redbud) grown as an ornamental tree for home and commercial landscapes. Redbud is typically grown as a small tree for its attractive purple flowers that are borne in the spring, and sometimes for its interesting foliage color (purple, variegated, or golden leaf forms).

This new and distinct variety of redbud resulted from a formal breeding program established by the inventors in Raleigh, N.C., United States. One of the objectives of the breeding program was to develop a double-flowered form of redbud that exhibited the foliage character and growth habit of the Texas redbud (small, glossy leaves and semi-upright growth habit). 'Pink Pom Poms' originated as a first generation descendant from open-pollinated seed collected in fall 2005 from a single tree of the double-flowered cultivar 'Flame' redbud, growing in a field setting in a commercial plant nursery in Belvidere, Tenn. Seed production on 'Flame' is highly unusual, as the double-flower trait is typically associated with female sterility. Adjacent to the 'Flame' tree was a tree of the cultivar 'Oklahoma'. The foliar and flower characteristics of 'Pink Pom Poms' are highly suggestive that the pollen parent of 'Pink Pom Poms' was 'Oklahoma'. 'Oklahoma' (unpatented) was released in late 1964, and is classified as a form of *Cercis canadensis* var. *texensis*. 'Flame' (unpatented) is a double-flowered form of eastern redbud (*Cercis canadensis*) discovered in 1905 in Illinois. Both parents are available in commerce.

The seeds resulting from the 2005 seed collection from 'Flame' were germinated in a greenhouse in Raleigh, N.C. in the winter of 2006. The resulting 278 seedlings were planted in a field in Jackson Springs, N.C., in spring 2006. Many of these plants flowered in summer 2008. From these 278 seedlings, one plant, designated NC2008-1, was selected for its glossy green leaf color, double flowers, attractive reddish-purple flower color, and semi-upright growth habit. This original plant demonstrated characteristics identical to those subsequently expressed in other plants of 'Pink Pom Poms' when propagated by chip budding. This single plant is the subject of the present invention 'Pink Pom Poms'.

The distinguishing traits of 'Pink Pom Poms' are its distinctive green glossy leaves, attractive purple-violet double flowers that are borne in abundance, semi-upright growth habit, and female structures that are essentially sterile. "Essentially sterile" is used because no seed pods have been observed to date; however, applicants do not preclude the possibility that a seed set may be observed on rare occasions. The cultural requirements for 'Pink Pom Poms' are well-drained soil, full sun, and moderate moisture. 'Pink Pom Poms' exhibits no serious pest or disease problems known to the inventors.

The closest comparison known to the inventors is the cultivar 'Flame' (unpatented), the female parent of 'Pink Pom Poms'. 'Flame' is currently the only double-flowered cultivar of redbud in commerce. Leaves and flowers of 'Pink Pom Poms' differ from 'Flame'. The leaves of 'Pink Pom Poms', have a distinct glossy appearance typical of its 'Oklahoma' pollen parent, whereas the leaves of 'Flame' have a dull green appearance. Flowers of 'Pink Pom Poms' are bright purple-violet (RHS N80A) in color, as compared to the purple color (RHS N78D) of 'Flame'. 'Pink Pom Poms' differs from its parent, 'Oklahoma', in having double flowers, compared to the single flowers of 'Oklahoma'. 'Pink Pom Poms' is also essentially female sterile, producing no seed pods, as compared to moderate female fertility and seedpod production of 'Oklahoma'. 'Pink Pom Poms' is clearly distinct from its parents, 'Flame' and 'Oklahoma'.

The first asexual propagation of 'Pink Pom Poms' was conducted in Belvidere, Tenn. in August, 2008 in Belvidere, Tenn. 'Pink Pom Poms' has subsequently been propagated in the same location in years 2010 and 2011. In all cases, the original plant selection was propagated asexually by chip budding in late summer onto *Cercis canadensis* rootstock. Such budded trees heal rapidly, and resume normal growth the following spring after budding. Five plants derived from chip budding of the variety in 2008 were established in test plots in Jackson Springs, N.C. in February, 2010. During all asexual propagation, the characteristics of the original plant have been maintained. Plants derived from chip budding exhibit characteristics identical to those of the original plant, and no aberrant phenotypes have appeared.

Performance evaluation of the original plant and budded trees for 8 years and 4 years, respectively, in Jackson Springs, N.C. demonstrate this variety to be relatively consistent in its characteristics even under the different growing conditions associated with yearly climatic variation.

Plants of the new variety are vigorous after establishment in the field, more so than most cultivars of redbud. The original plant is 4.1 meters in height after 8 years of growth, an average of 0.51 meters of growth per year. Plants are semi-upright in growth habit. Flowering typically occurs on previous season's growth in the second year after budding. The flower is double, and shows a bright purple-violet flower color. Flowering usually begins in early April in Jackson Springs, N.C., and typically continues through mid to late April, depending on weather conditions. An individual flower persists for about 10 days, depending on the temperature. 'Pink Pom Poms' is essentially female sterile. In 8 years of evaluation, no seedpods have ever been produced on the original tree or chip-budded trees. This is considered an important asset in landscape settings.

'Pink Pom Poms' is distinguished from other related known cultivars based on the unique combination of traits including high vigor, semi-upright growth habit, glossy leaf character, abundant production of double flowers having a bright purple-violet color, and female structures that are essentially sterile.

SUMMARY OF THE INVENTION

'Pink Pom Poms' is a new and distinct variety of redbud that has the following unique combination of desirable features outstanding in a new variety. In combination, these traits set 'Pink Pom Poms' apart from all other existing varieties of redbud known to the inventors.

1. 'Pink Pom Poms' has high vigor resulting in larger tree size than the typical eastern redbud.
2. 'Pink Pom Poms' is asexually propagated using chip budding.
3. 'Pink Pom Poms' demonstrates semi-upright growth habit.
4. 'Pink Pom Poms' has attractive glossy-green leaves.
5. 'Pink Pom Poms' is essentially female sterile and has produced no seed pods to date.
6. 'Pink Pom Poms' has bright purple-violet double flowers.

BRIEF DESCRIPTION OF THE DRAWINGS

This new redbud is illustrated by the accompanying photographs which show the plant's foliage and inflorescences. The colors shown are as true as can be reasonably obtained by digital photography. Colors in the photographs may differ slightly from the color values cited in the detailed botanical description, which accurately describes the colors of the new *Cercis* variety 'Pink Pom Poms'. All photographs were taken from the original tree growing at Jackson Springs, N.C.

DETAILED BOTANICAL DESCRIPTION

Figure 1:
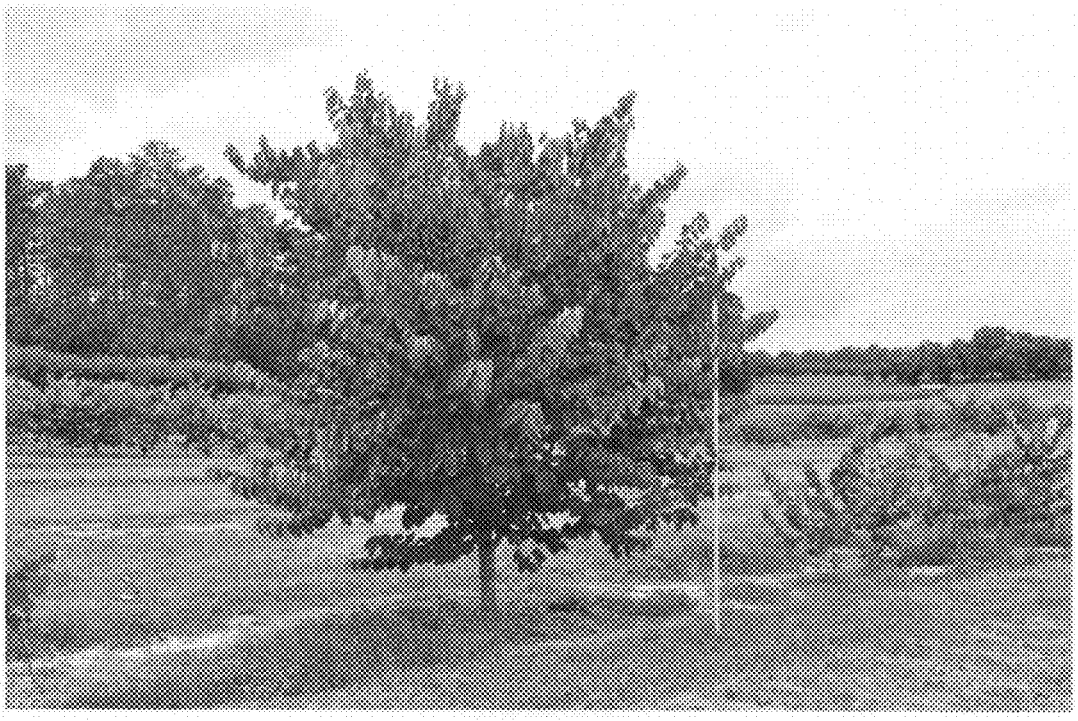
FIG. 1 is a color photograph of the original tree of 'Pink Pom Poms' taken in July 2012 (seven years old) showing the vigorous growth, and semi-upright habit.
Figure 2:
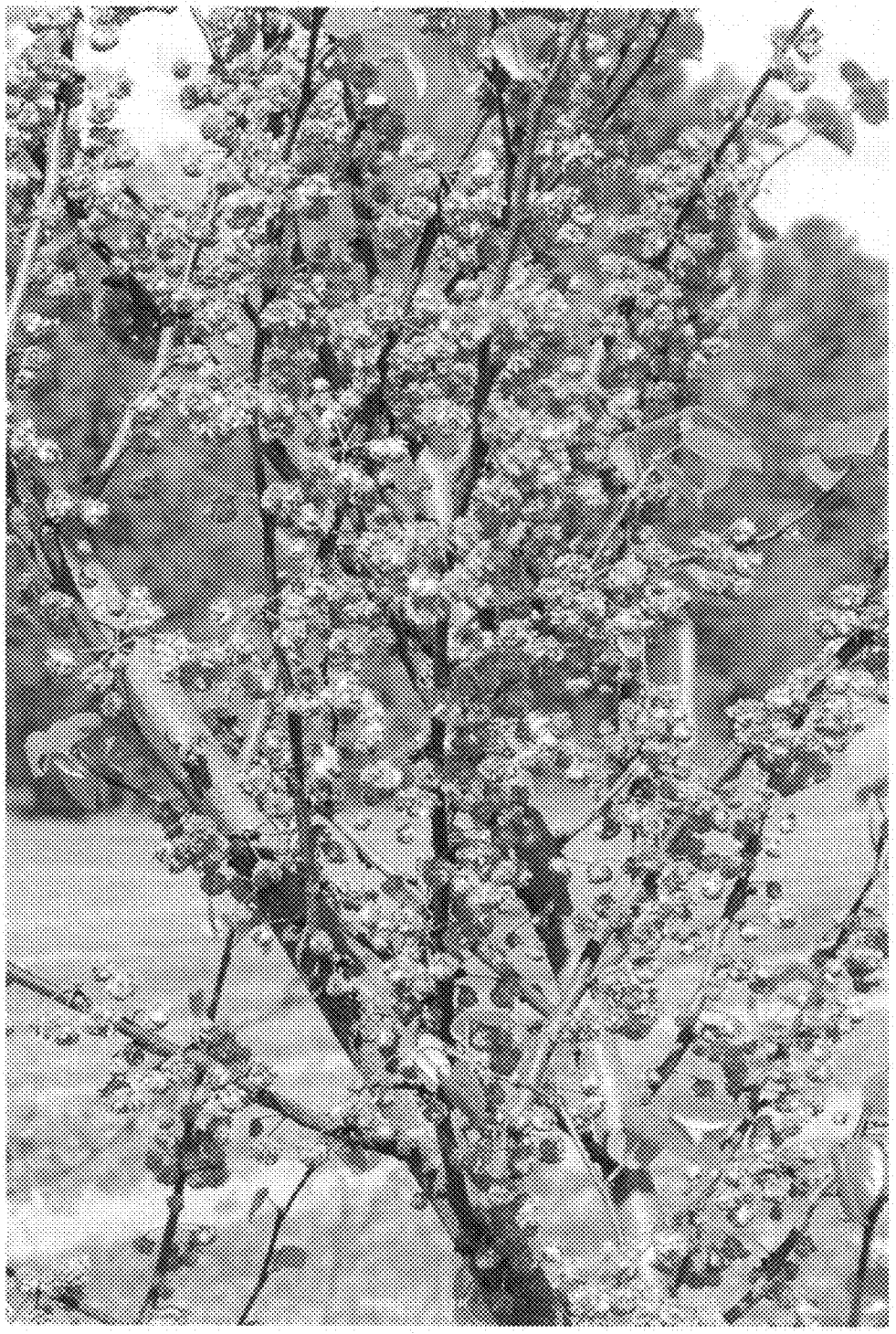
FIG. 2 is a color photograph of a branch of 'Pink Pom Poms' in full flower showing the bright, purple-violet color of the double flowers. The photograph was taken in April 2010 when the tree was five-years old.
Figure 3:
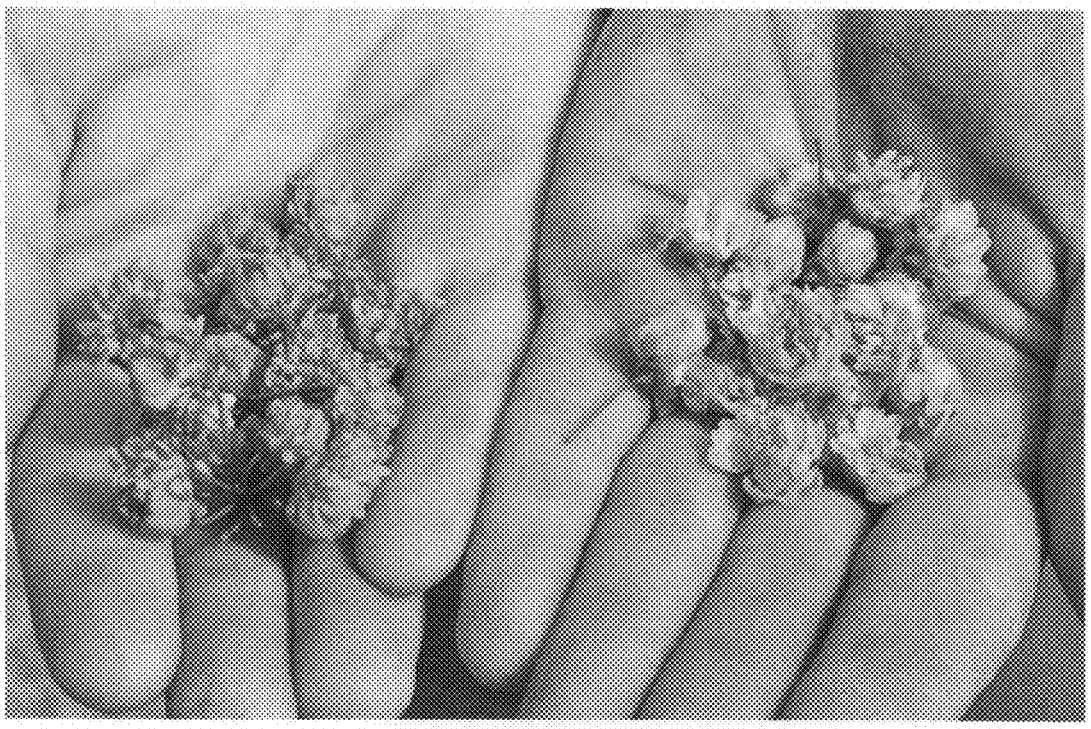
FIG. 3 shows a comparison of the flower color of 'Pink Pom Poms' (left) vs. 'Flame' (right). The photograph was taken in March 2012 when the tree was seven years old.
Figure 4:
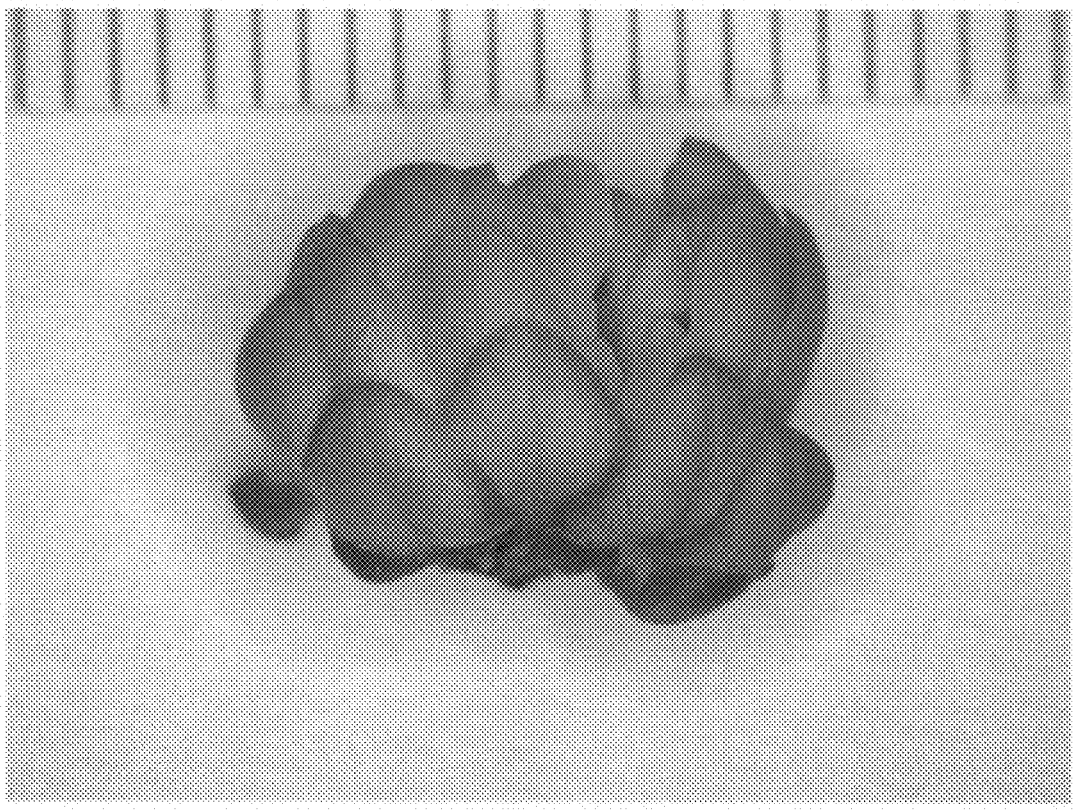
FIG. 4 shows a close-up of an individual flower of 'Pink Pom Poms' taken in April 2013.
Figure 5:
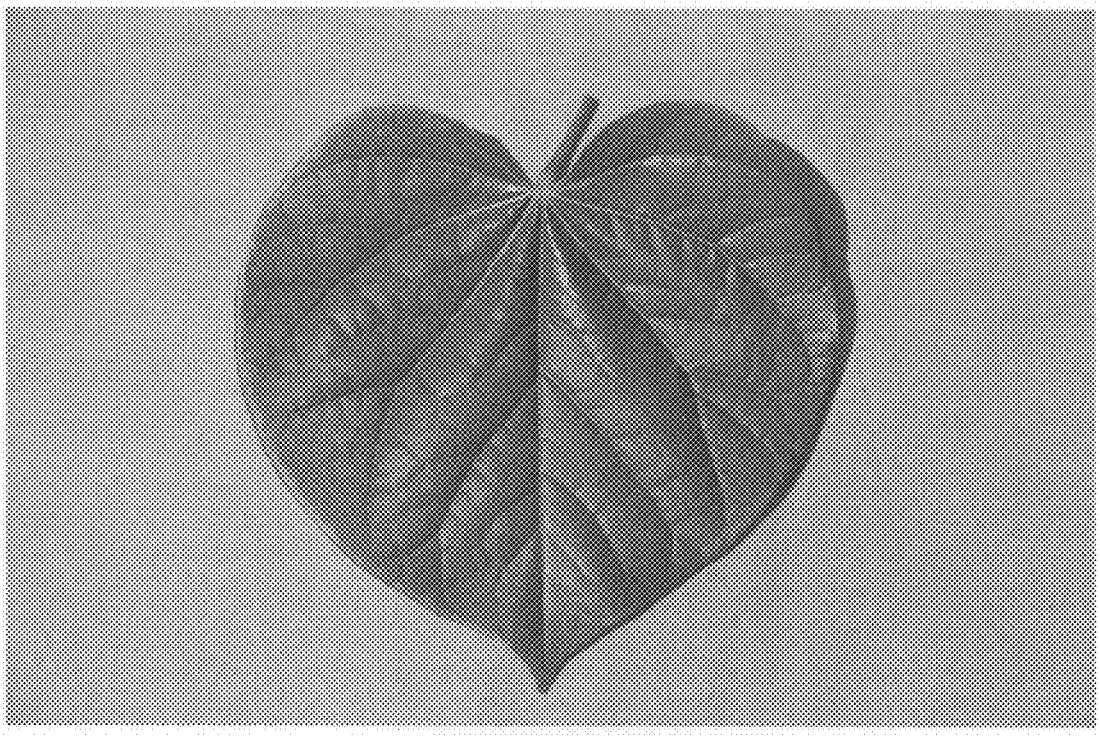
FIG. 5 provides a close-up of a leaf of 'Pink Pom Poms' taken in April 2013 from the original eight year old tree. The photograph shows the typical coloration, glossiness, and form of a leaf of 'Pink Pom Poms'.

The following is a detailed description of the botanical and ornamental characteristics of the subject redbud 'Pink Pom Poms'. Color data are based on *The Royal Horticultural Society Colour Chart,* The Royal Horticultural Society, London, 2007 edition. Where dimensions, sizes, colors and other characteristics are given, it is to be understood that such characteristics are approximations of averages set forth as accurately as practicable.

The descriptions reported herein are from the original eight-year-old tree growing at the research station in Jackson Springs, N.C.

Genus: *Cercis.*

Species: Hybrid between *canadensis* and *canadensis* var. *texensis.*

Denomination: 'Pink Pom Poms'.

Commercial classification: Tree, deciduous.

Common name: Redbud.

Type: Ornamental.

Uses: Small landscape tree for residential and commercial landscapes.

Cultural requirements: Full to part-sun exposure, well-drained soil, and moderate moisture.

Parentage: 'Pink Pom Poms' is a first-generation offspring that resulted from the open-pollination of *Cercis canadensis* (eastern redbud) 'Flame'. The putative male (pollen) parent is 'Oklahoma' (*Cercis canadensis* var. *texensis*), the Texas redbud.

Plant description:

*Blooming period.*—Early to mid spring, early to mid April in south-central North Carolina.

*Blooming habit.*—Flower buds are formed both on one-year-old wood and on older wood.

*Vigor.*—High vigor.

*Plant habit.*—Dense growth, semi-upright to slightly spreading growth habit.

*Height and spread.*—4.1 meter height and 3.9 meter spread on original eight-year-old tree.

*Hardiness.*—To date, hardy to negative 12.8 degrees Centigrade; not tested below this temperature; anticipated to be adapted to USDA hardiness zones 6-9.

*Propagation.*—Chip-budding onto seedling rootstock, typically in late summer in the southeastern U.S.

*Root system.*—Fibrous.

*Seasonal interest.*—Bright purple-violet flowers in spring, and glossy green leaves from spring throughout the growing season.

*Disease and pest susceptibility and resistance.*—No particular susceptibility or resistance.

*Special growing requirements.*—None; best grown in full sun to partial shade in moderately well drained soil.

Trunk:

*Dimensions.*—15.5 cm circumference measured 0.15 m above soil line.

*Bark surface.*—Slightly rugose.

*Color.*—Lighter sectors are blue-green (RHS 122D). Darker sectors are greyed-green (RHS 188A).

Stems:

*Shape.*—Stem cross section is circular.

*Length.*—Average 52.1 cm per year of growth.

*Color.*—Purple (RHS N77A) on recently formed new growth; brown (RHS N200A) on dormant one and two-year-old stems.

*Diameter.*—8 mm near terminal portion of stem on mature one-year-old stems.

*Stem surface.*—Glaucous.

*Pubescence.*—Lacking.

*Internode length.*—3 cm between nodes.

*Lenticels.*—Numerous, tiny; color brown (RHS N200B).

*Lenticel shape.*—Circular.

*Lenticel size.*—1 mm or less diameter.

Foliage:

*Type.*—Deciduous.

*Leaf arrangement.*—Alternate.

*Leaf division.*—Simple.

*Leaf shape.*—Suborbicular (immature) to broad-ovate (mature).

*Leaf base.*—Cordate.

*Leaf apex.*—Obtuse to slightly pointed.

*Leaf venation.*—Reticulate.

*Leaf surface (abaxial and adaxial).*—Glaucous.

*Leaf margin.*—Entire.

*Leaf attachment.*—Petiolate.

*Petiole dimensions.*—3.1 cm length; 2.6 mm width at base tapering to 1 mm at apex (nearest to leaf blade).

*Petiole shape.*—Round.

*Petiole color.*—Green (RHS 138C).

*Petiole surface.*—Smooth, lacking pubescence.

*Leaf color (immature leaf).*—Adaxial side is yellow-green (RHS Green 140B). Abaxial side is yellow-green (RHS Green 140B).

*Leaf color (mature leaf).*—Adaxial side is green (RHS 137A). Abaxial side is green (RHS 138A).

*Vein color (abaxial surface).*—Green (RHS 138D).

*Leaf length.*—10.3 cm from leaf tip to base of midvein/apex of petiole. 12.7 cm from leaf tip to base of leaf blade.

*Leaf width.*—12.6 cm.

*Foliar fragrance.*—None detectable.

*Stipules.*—None present.

Flowers:

*Inflorescence.*—Double flowers arranged in a small cluster (fascicle).

*Flower type.*—Double flower (vs. typical single flower of redbud).

*Number of flowers per cluster.*—7 to 11; average=8.8.

*Arrangement.*—Sessile clusters.

*Location.*—Nodes of previous year's growth, and along older stems and occasionally the trunk (cauliflory).

*Length of bloom.*—2-3 weeks, depending on weather conditions.

*Flower length.*—9.2 mm from base of calyx to tip.

*Flower width.*—15 mm at anthesis.

*Pedicel length.*—12.6 mm.

*Pedicel diameter.*—1 mm.

*Pedicel shape.*—Round.

*Pedicel color.*—Red-purple (RHS 59A).

*Pedicel surface.*—Smooth.

*Flowers persistent or self-cleaning.*—Self-cleaning.

*Flower fragrance.*—Lacking.

*Lastingness of the overall inflorescence.*—2-3 weeks.

*Lastingness of an individual flower.*—5-7 days.

Flower bud:

*Shape.*—Broadly oval.

*Color.*—Purple (RHS N77A).

*Surface.*—Smooth.

*Diameter.*—1.5 to 2 mm.

*Length.*—2 mm.

Petals:

*Number.*—35 per flower.

*Petals fused or unfused.*—Unfused.

*Petal color.*—Purple-violet (RHS N80A).

*Petal surface (adaxial).*—Smooth.

*Petal surface (abaxial).*—Smooth.

*Petal margin.*—Entire.

*Petal length.*—6.9 mm.

*Petal width.*—4.5 mm.

Calyx:

*Shape.*—Vase-shaped.

*Length.*—4 mm.

*Diameter.*—5 mm.

*Color (outer surface).*—Red-purple (RHS 71A).

*Color (inner surface).*—Red-purple (RHS 71A).

*Surface (inner).*—Smooth.

*Surface (outer).*—Smooth.

Sepals:

*Number.*—5 — fused.

*Color (adaxial surface).*—Red-purple (RHS 71A).

*Color (abaxial surface).*—Red-purple (RHS 71A).

*Surface (adaxial surface).*—Smooth.

*Surface (abaxial surface).*—Smooth.

Reproductive organs:

*Pistil.*—Dimensions: 1 cm length; <1 mm width; often malformed. Color: Red-purple (RHS 59B). Surface: Smooth. Function: Non-functional; essentially female sterile.

*Stigma.*—Shape: Round. Length: Less than 1 mm. Width: Less than 1 mm. Color: Red-purple (RHS 60D).

*Style*.—Shape: Elongate. Length: Less than 1 mm. Width: Less than 1 mm. Color: Red-purple (RHS 60D).

*Stamens*.—Number: Variable; absent to 2 per flower. Fused or unfused at base: Unfused. Length: 8 mm. Width: Less than 1 mm. Color (filament): Red-purple (RHS 63B).

*Anthers*.—Shape: Round to slightly oblong; many distorted and non-functional. Length: Less than 1 mm. Width: Less than 1 mm. Color: Red-purple (RHS 64B); immediately prior to anthesis.

*Pollen*.—Color: Yellow (RHS 9B). Amount: Lacking to very sparse.

*Ovary*.—Position: Superior. Shape: Elongate. Length: 8.4 mm. Width: 1 mm. Color: Yellow-green (RHS N144C).

*Fruit*.—Type: None observed in 8 years of observation. Arrangement: N.A. Color: N.A. Seed: None produced to date, likely due to double flowered trait of 'Pink Pom Poms'.

Herbarium voucher: A voucher of 'Pink Pom Poms' will be deposited into the Herbarium of North Carolina State University (NCSU) in Raleigh, N.C., USA upon patenting.

What is claimed is:

1. A new and distinct variety of redbud tree (*Cercis*) named 'Pink Pom Poms' having the characteristics substantially as described and illustrated herein.

* * * * *